United States Patent
Jönsson

(10) Patent No.: US 10,639,153 B2
(45) Date of Patent: May 5, 2020

(54) DELIVERY DEVICE FOR MEDICAL IMPLANT AND MEDICAL PROCEDURE

(71) Applicant: AEEG AB, Helsingborg (SE)

(72) Inventor: Anders Jönsson, Bromma (SE)

(73) Assignee: AEEG AB (SE)

( * ) Notice: Subject to any disclaimer, the term of this patent is extended or adjusted under 35 U.S.C. 154(b) by 212 days.

(21) Appl. No.: 15/430,215

(22) Filed: Feb. 10, 2017

(65) Prior Publication Data

US 2017/0216030 A1    Aug. 3, 2017

Related U.S. Application Data

(63) Continuation of application No. 14/236,603, filed as application No. PCT/EP2012/062931 on Jul. 3, 2012, now abandoned.

(Continued)

(51) Int. Cl.
*A61B 17/24* (2006.01)
*A61B 34/10* (2016.01)
*A61F 2/24* (2006.01)

(52) U.S. Cl.
CPC ............ *A61F 2/2445* (2013.01); *A61B 34/10* (2016.02); *A61F 2/2466* (2013.01);
(Continued)

(58) Field of Classification Search
CPC .... A61F 2/2433; A61F 2/2436; A61F 2/2442; A61F 2/2445; A61F 2/2448
See application file for complete search history.

(56) References Cited

U.S. PATENT DOCUMENTS 6,626,930 B1    9/2003   Allen et al.
7,335,213 B1 *  2/2008   Hyde ................. A61B 17/0469
                                                    606/151
(Continued)

FOREIGN PATENT DOCUMENTS

DE    102007043831 A1    4/2009
EP       0624342 A1     11/1994
(Continued)

OTHER PUBLICATIONS

WIPO, European International Preliminary Examining Authority, International Preliminary Report on Patentability dated Oct. 7, 2013 in International Patent Application No. PCT/EP2012/062931, 21 pages.

(Continued)

*Primary Examiner* — Tuan V Nguyen
(74) *Attorney, Agent, or Firm* — Thomas | Horstemeyer, LLP

(57) ABSTRACT

A catheter (4) based medical system (1) and medical procedure for reducing cardiac valve regurgitation are disclosed. The system comprises a resilient curvilinear shaped annuloplasty implant (3) for reducing the size of a dilated annulus (18) of said valve for reducing said regurgitation having resilient anchoring elements (300), and a delivery device (2) for said annuloplasty implant (3) having a distal curvilinear shaped portion (200) that is hollow to mount said annuloplasty implant (3) and has an annular opening (201) arranged to be in apposition against an annulus (18) of said cardiac valve. A plurality of suction units allows for a atrial approach and symmetric implantation of said implant.

7 Claims, 4 Drawing Sheets

Related U.S. Application Data

(60) Provisional application No. 61/514,693, filed on Aug. 3, 2011.

(52) U.S. Cl.
CPC ... *A61B 2034/104* (2016.02); *A61B 2034/108* (2016.02); *A61F 2220/0008* (2013.01); *A61F 2250/0096* (2013.01)

(56) References Cited

U.S. PATENT DOCUMENTS

| | | |
|---|---|---|
| 2006/0212114 A1 | 9/2006 | Menicnti et al. |
| 2007/0244552 A1* | 10/2007 | Salahieh ............... A61F 2/2418 623/2.11 |
| 2010/0198346 A1* | 8/2010 | Keogh .................... A61N 7/02 623/2.11 |

FOREIGN PATENT DOCUMENTS

| | | |
|---|---|---|
| EP | 2351540 A1 | 8/2011 |
| WO | WO2011/031733 A2 | 3/2011 |
| WO | WO2011/092267 A1 | 8/2011 |

OTHER PUBLICATIONS

WIPO, European International Search Authority, International Search Report dated Oct. 26, 2012 in International Patent Application No. PCT/EP2012/062931, 6 pages.

\* cited by examiner

DELIVERY DEVICE FOR MEDICAL IMPLANT AND MEDICAL PROCEDURE

CROSS-REFERENCE TO RELATED APPLICATION

This application is a continuation of copending U.S. utility application entitled "Delivery Device for Medical Implant and Medical Procedure" filed on Feb. 19, 2014, having Ser. No. 14/236,603, which claims priority to International Patent Application No. PCT/EP2012/062931, International Filing Date Jul. 3, 2012, entitled "Delivery Device For Medical Implant And Medical Procedure", which claims benefit of U.S. Provisional Application Ser. No. 61/514,693, filed Aug. 3, 2011 entitled "Delivery Device For Medical/Implant And Medical Procedure"; which are incorporated herein by reference in their entireties.

FIELD OF THE INVENTION

This invention pertains in general to the field of medical devices and methods. More particularly the invention relates to cardiac valve repair devices and methods, and even more particularly to a system of cardiac valve annuloplasty implants and corresponding delivery tools for said implants, as well as associated methods and procedures.

BACKGROUND OF THE INVENTION

The human heart is a hollow muscular organ having four pumping chambers separated by four heart valves. The mitral and tricuspid valves, present at the left and right atrio-ventricular junctions, open and close in response to a pressure gradient during each cardiac cycle of relaxation and contraction to control the flow of blood to a particular region of the heart.

These valves are comprised of a dense fibrous ring known as the annulus, leaflets or cusps attached to the annulus, and a complex of chordae tendinae and papillary muscles securing the leaflets. The size of the leaflets or cusps is such that when the heart contracts the resulting increased blood pressure formed within the ventricular cavity forces the leaflets towards the arterial cavity. As a result, the leaflets or cusps come in apposition to each other thereby closing the atrio-ventricular passage.

Natural defects and heart disease are common causes of valvular dysfunction within the heart of a patient. One common example of valvular dysfunction occurs, when the annulus becomes excessively dilated or the valve geometry results in ineffective valve closure, which results in regurgitation. Due to the increased diameter of the annulus, the leaflets or cusps fail to meet during systolic contraction, thereby resulting in the regurgitation of blood during ventricular contractions. As such, sufficient back pressure exists within the chambers of the heart capable of forcing some blood flow to traverse the atrio-ventricular junction from the ventricle to the atria.

One manner of repairing this problem involves surgically implanting a prosthetic implant, often referred to as "annuloplasty rings", about the dilated annulus, thereby restoring the annulus to the normal size and shape and allowing the valve leaflets to function normally. Commonly, a surgeon positions the annuloplasty ring near the valve annulus and sutures the device in place.

One approach to correcting or remodelling the valve annulus has required the implantation of a rigid annuloplasty ring. Typically, an annuloplasty ring having the desired internal diameter is positioned near the heart valve and sutured in place. As a result, the diameter of the valve is reduced to the diameter of the annuloplasty ring.

The previously published US patent application 2005/055087 A1, describes methods for "Introducing a stabilizing member beneath one or more heart leaflets" in-conjunction with an optional "Second stabilizing member . . . introduced above the (valve) leaflets for further stabilization". A catheter is utilised to deliver the stabilizing member(s), as well as "Hydraulically driven tethered anchors" which provide for cinching of the dilated annulus, through adjustment of the tether. The anchors are separate entities not attached to the tether. The tether is merely guided in an eyelet of each of the anchors. An annuloplasty ring is not described. After deployment, the device is not retrievable from the patient other than by open chest surgery. This may be a major disadvantage when the device is malpositioned.

In US 2007/0016287 an "Implantable device is provided for controlling shape and/or size of an anatomical structure or lumen." Wherein the implantable ring utilises an adjustment means to regulate the size of the annulus and is attached to the tissue through drawing of a deployment suture which releases tissue anchors which previously were flush to the annulus. The number of anchor elements is limited as the total number of anchor elements is defined by the specific length of each of the adjacent anchoring elements when flush. This also means that the maximum anchoring depth of the anchor when released is limited. Thus, there is a need to improve reliability of anchoring. Moreover, the annuloplasty ring may not comprise a collar element around the ring, sometimes desired to improve sealing of the ring against the annulus, as the anchors would be hindered from their movement. After deployment, the device is not retrievable from the patient other than by open chest surgery. This may be a major disadvantage when the device is malpositioned.

Although these provide possible treatment modalities, improved treatment means are required to provide enhanced tissue attachment in-conjunction with greater ease of regulating annular size to limit the procedure time and safeguard against misplacement which can lead to e.g. embolization.

Catheter based delivery via an atrial approach would be desired to avoid interference with the subvalvular apparatus.

An automated annuloplasty procedure or device/system allowing this would be desired.

A symmetrical reshaping of the annulus by a device would be desired.

Open chest surgery or other invasive procedures, like intercostal transapical cardiac access paths are desired to be avoided.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical system, procedures and methods, according to the appended patent claims.

In an aspect, a catheter based medical system is disclosed. The system includes a retractable delivery device for delivery of a medical implant, such as an annuloplasty implant (3) for reducing cardiac valve regurgitation. The delivery device having a distal portion for releasably holding the implant, and for apposition against a target tissue for the implant, such as an annulus (18) of a cardiac valve. The distal portion comprises a plurality of suction units for providing and/or determining a desired apposition of the distal portion at the target tissue prior to releasing the medical implant to the tissue and retracting the delivery device.

Advantageously, the suction units are provideable with a negative pressure for suction to the tissue, and wherein the medical implant is not releasable before all suction units are confirmed in apposition with the tissue.

Advantageously, the plurality of suction units are distributed along a periphery of the distal portion.

Advantageously, a firm seat at the tissue is confirmed by an absence of a reflow of blood from the suction units.

Advantageously, the suction units are arranged to provide for a symmetric delivery of the implant when release to the tissue.

Advantageously, the tissue is a cardiac valve annulus and the implant is an annuloplasty implant, such that the distal portion is arrangeable for a synchronous and simultaneous reshaping procedure of the annulus by the implant.

Advantageously, apposition of the suction units is measurable based on a signal for a pressure in the suction unit an energy consumption of a flow generator generating the pressure.

Advantageously, the distal portion has arranged thereon a plurality of sensors for indicating contact with the annulus tissue, such as piezo transducers.

The cardiac valve may be a mitral valve, and wherein the system is adapted for transseptal percutaneous delivery into the left atrium to the atrial side of the mitral valve, and wherein the delivery portion of the delivery device is distally connected to the distal portion and has a distal curvature to allow access from a septal opening towards the mitral valve.

The cardiac valve may be a tricuspid valve, and wherein the system is adapted for percutaneous delivery into the right atrium to the atrial side of the tricuspid valve, and wherein the delivery portion of the delivery device is distally connected to the distal portion and has a distal curvature to allow suitable access towards the tricuspid valve.

In this manner, the subvalvular apparatus is avoided during delivery. Delivery is made from the atrial side of the cardiac valve. Open chest surgery, or intercostal delivery, and/or transapical delivery is avoided.

Advantageously, the implant is a resilient curvilinear shaped annuloplasty implant that has a tissue engaging conformation based on a desired downsized shape where the regurgitation of the valve is reduced. The distal portion has a delivery conformation based on a shape of the dilated valve annulus shape, wherein the delivery conformation has a dimension that is larger than the tissue engaging conformation of the annuloplasty implant, such that the annuloplasty implant is resiliently kept in the delivery conformation before release from the distal portion. Advantageously, the distal portion has at least one fiducial marker, wherein the fiducial marker is preferably arranged at a periphery of the distal portion. One of the fiducial markers may be an annular fiducial marker arranged along the periphery. A plurality of fiducial markers may be distributed along the distal curvilinear shaped portion for identifying the distal curvilinear shaped portion inside a body of a patient having the cardiac valve. A trace of a plurality of fiducial markers gives a 3D identifiable position.

Advantageously, the fiducial markers include an air inclusion for detection by ultrasound.

In another aspect, a medical procedure is disclosed. The procedure is provided for reducing cardiac valve regurgitation. The method may include the following steps, namely measuring the geometry of a dilated cardiac valve of a patient including the shape and size of a dilated annulus thereof; determining the downsized shape and size of the annulus; selecting a resilient annuloplasty implant having in a tissue engaging conformation a shape and size to be arranged at the downsized annulus based on the determined downsized shape and size of the annulus; introducing the annuloplasty implant in a delivery device in a compressed state via a catheter to the cardiac valve; releasing an aggregate of a distal portion of the delivery device and the annuloplasty implant in a stretched state in the delivery device from the catheter such that implant assumes an expanded shape; positioning the aggregate at the annulus; fixation the distal portion to the annulus, e.g. by activating suction of suction units; providing and/or verifying a desired apposition of the distal portion at the annulus prior to releasing the implant; releasing and anchoring the annuloplasty implant into the annulus; reducing the size of the delivery device and/or annuloplasty implant for reshaping the annulus to the downsized shape; optionally determining a reduction of the cardiac valve regurgitation, and removing the delivery device and catheter if the reduction is satisfactory, or removing the annuloplasty implant together with the delivery device when the reduction is determined as not being satisfactory.

Advantageously, the procedure includes ultrasonic measurement for the measuring the geometry of the dilated cardiac valve, and/or the determining a reduction of the cardiac valve regurgitation.

Advantageously, the procedure includes applying a catheter based medical system for reducing the cardiac valve regurgitation, having the resilient curvilinear shaped annuloplasty implant for reducing the size of a dilated annulus of the valve for reducing the regurgitation, and a delivery device for the annuloplasty implant having a distal portion receiving the annuloplasty implant and has an opening arranged to be in apposition against an annulus of the cardiac valve. The procedure may include further releasably mounting the annuloplasty implant in the hollow with the resilient anchoring elements arranged in a restrained spring loaded delivery conformation in the hollow, for the introducing; positioning the aggregate at the annulus; fixation the distal portion to the annulus, e.g. by activating suction of suction units; providing and/or verifying a desired apposition of the distal portion at the annulus prior to releasing the implant; releasing and anchoring the annuloplasty implant into the annulus.

Advantageously, the procedure includes restraining the annuloplasty implant in a hollow of the distal portion with a second restraining unit, and releasing the annuloplasty implant from the hollow upon releasing the second restraining unit, wherein the second restraining unit preferably is only released when a correct position of the annuloplasty implant is confirmed, allowing for removing the annuloplasty implant from the annulus if the correct positioning of the annuloplasty implant is not confirmed, and avoiding undesired embolization of the annuloplasty implant.

Advantageously, the procedure includes making a transseptal puncture in the heart; wherein the cardiac valve is a mitrel valve, and wherein the introducing is a transseptal percutaneous delivery into the left atrium to the atrial side of the mitral valve, and wherein a delivery portion of the delivery device is distally connected to the distal curvilinear shaped portion and has a distal curvature to allow access from a septal opening towards the mitral valve.

Advantageously, the procedure includes making a transseptal puncture in the heart; wherein the cardiac valve is tricuspid valve, and wherein the system is adapted for percutaneous delivery into the right atrium to the atrial side of the tricuspid valve, and wherein a delivery portion of the delivery device is distally connected to the distal curvilinear shaped portion and has a distal curvature to allow suitable access towards the tricuspid valve.

Catheter access to the left atrium is e.g. achieved by positioning a catheter in central or peripheral veins, thereby achieving access to the right atrium. In such a situation, the tricuspid valve may be accessed from above the valve. Then a standard atrial trans-septal approach may be utilized to access the left atrium by creation of an iatrogenic atrial septal defect (ASD). In such a situation, the mitral valve may be accessed from above the valve, see FIG. 3.

Advantageously, the procedure includes generating a negative pressure in suction units of the distal portion for suction of the distal portion to the annulus.

Advantageously, the procedure includes measuring the negative pressure and determining a contact of the suction units(s) with the annulus tissue from the measured pressure or an energy consumption of a flow generator generating the pressure.

Advantageously, the procedure includes indicating contact with the annulus tissue with a sensor arranged on the distal portion, such as based on sound waves emitted and received from a piezo transducer, such as an ultrasonic transducer.

Advantageously, the procedure includes identifying the distal portion inside a body of a patient having the cardiac valve by means of detecting at least one fiducial marker of the delivery device, such as a plurality of fiducial markers distributed along the distal portion for the identifying and/or a fiducial marker that is arranged at a periphery of the distal portion, and/or wherein one of the fiducial markers is an annular fiducial marker arranged along the periphery.

In another aspect, a method of virtually planning an annuloplasty implantation is disclosed for a medical procedure. The method comprises, in a computer environment, image based, such as ultrasonic based, measuring a geometry of a dilated cardiac valve from patient image data, and determining a reduction of a regurgitation of the valve when downsizing the annulus of the dilated valve; selecting a patient adapted shape and size of a resilient annuloplasty implant, such as described herein, for a tissue engaging conformation to be arranged at the downsized annulus based on the determined downsized shape and size of the annulus; and providing production data for the device and/or a delivery system thereof.

Advantageously, the method includes measuring the geometry of a dilated cardiac valve of a patient including the shape and size of a dilated annulus thereof, and the determining the downsized shape and size of the annulus are made in a computer based, virtual environment.

In another aspect, a method of producing a medical device is disclosed from production data obtained by the virtual planning of the afore aspect.

A medical device may be provided for reducing cardiac valve regurgitation. The device includes an elongate resilient curvilinear shaped annuloplasty implant for reducing the size of a dilated annulus of the valve for reducing the regurgitation. The annuloplasty implant has resilient anchoring elements protruding radially outwards from the annuloplasty implant. The anchoring elements are arrangeable in a spring loaded first radial direction for delivery, and when released from the delivery position anchor the annuloplasty implant to tissue at the annulus in a second radial direction, different from the first radial direction.

Multiple of the anchoring elements may be arranged at different radial positions around the cross section of the annuloplasty implant. The anchoring elements may preferably be arranged opposite each other. The anchoring elements may preferably be arranged at the same longitudinal position on the annuloplasty implant.

According to another aspect, a system is disclosed provided, namely a catheter based medical system for reducing cardiac valve regurgitation, comprising a resilient and/or elastic curvilinear shaped annuloplasty implant for reducing the size of a dilated annulus of the valve for reducing the regurgitation having resilient anchoring elements; a delivery device for the annuloplasty implant having a distal curvilinear shaped portion that is hollow in which to mount the annuloplasty implant and has an annular opening arranged to be appositioned against an annulus of the cardiac valve; wherein the annuloplasty implant is releasably mounted in the hollow and has the resilient anchoring elements arranged in a restrained spring loaded delivery conformation in the hollow, and wherein the resilient anchoring elements when released from the restraining unit are arranged in a tissue engaging conformation protruding out of the opening.

The system is minimally invasive deliverable via a transluminal catheter.

Advantageously, the resilient elastic curvilinear shaped annuloplasty implant has a tissue engaging conformation based on a desired downsized shape where the regurgitation of the valve is reduced, and the distal curvilinear shaped portion has a delivery shape based on a shape of the dilated valve annulus shape, wherein the delivery shape has a dimension that is larger than the relaxed shape of the annuloplasty implant, such that the annuloplasty implant is resiliently mounted in the hollow in the delivery shape before being released from the hollow.

The annuloplasty implant may be of a closed ring shape. The ring may be round or oval in shape. Alternatively, the annuloplasty implant may be of an interrupted ring shape, such as a C-shape. The cross section of the elongate member forming the (partial) ring may be circular, flattened, oval, or have other shapes suitable for apposition to the annulus tissue. The implant may have a shape with a desired 3D topography.

Advantageously, the delivery device has a sizing actuator, and wherein the distal curvilinear shaped portion is reducible from the delivery shape by the actuator.

Advantageously, the delivery device has a first restraining unit for restraining the anchoring elements in the restrained spring loaded delivery position.

Advantageously, the delivery device has a second restraining unit for restraining the annuloplasty implant in the hollow of the distal curvilinear shaped portion. The restraining unit is e.g. a tether line. In this manner, additional security is provided as the implant may be retracted when it is still mounted in the delivery device. Thus e.g. embolization of the device is avoided, which otherwise would make a surgical retrieval procedure necessary, likely including open chest surgery with all its disadvantages.

Advantageously, the delivery device has a third restraining unit for keeping the annuloplasty implant in the hollow of the distal curvilinear shaped portion.

Advantageously, the system has a first, second and third restraining unit, wherein the third restraining unit is arranged to release the annuloplasty implant by withdrawing the delivery device when the first restraining unit has released the anchoring elements from the restrained spring loaded delivery conformation and anchored the anchoring elements into the annulus tissue.

Advantageously, the hollow of the distal curvilinear shaped portion is of a fluid impermeable material. Thus it may be provided with a negative pressure for suction of the hollow to the annulus. In some embodiments a pressure in the hollow is measured and a contact with the annulus tissue is determinable from the measured pressure or an energy consumption of a flow generator generating the pressure.

Advantageously, the distal curvilinear shaped portion has arranged thereon a sensor for indicating contact with the annulus tissue, such as a piezo transducer.

Advantageously, the distal curvilinear shaped portion has at least one fiducial marker. The fiducial marker may be arranged at a periphery of the distal curvilinear shaped portion; and/or wherein one of the fiducial markers is an annular fiducial marker arranged along the periphery. A plurality of fiducial markers may be distributed along the distal curvilinear shaped portion for identifying the distal curvilinear shaped portion inside a body of a patient having the cardiac valve.

After positioning the aggregate at the annulus the position of the aggregate relative the annulus may be validated and adjusted if deemed necessary. This provides for flexibility and reliability of deployment of the aggregate.

As the annuloplasty implant may be retrieved, together with the delivery device, even after releasing the anchor elements, the procedure provides for retrievability of the implant in a manner that hitherto was not possible.

Advantageously, delivery of a patient adapted annuloplasty curvilinear shaped structure is provided. Patient adaptation of the device may be based on imaging data of the dilated valve structure. The shape of the device, number of anchoring elements, depth of anchoring elements, etc. is chosen to effectively treat the valve leakage.

Advantageously, the procedure includes image based measurement, such as ultrasonic measurement, for the measuring a geometry of the dilated cardiac valve, and/or the determining a reduction of the cardiac valve regurgitation.

Advantageously, the procedure further includes subsequently to the positioning the aggregate at the annulus: determining a position of the delivery device at the annulus, and repositioning the delivery device and annuloplasty implant.

Advantageously, the procedure includes applying a catheter based medical system for reducing the cardiac valve regurgitation, having the resilient curvilinear shaped annuloplasty implant for reducing the size of a dilated annulus of the valve for reducing the regurgitation having resilient anchoring elements, and a delivery device for the annuloplasty implant having a distal curvilinear shaped portion that is hollow to mount the annuloplasty implant and has an annular opening arranged to be appositioned against an annulus of the cardiac valve; the procedure comprising mounting the releasable annuloplasty implant in the hollow with the resilient anchoring elements arranged in a restrained spring loaded delivery position in the hollow, for introducing and releasing; and releasing the resilient anchoring elements and arranging the resilient anchoring elements in a tissue engaging conformation protruding out of the opening of the annulus for the releasing.

Advantageously, the procedure is a minimally invasive procedure.

Advantageously, the resilient curvilinear shaped annuloplasty implant has a tissue engaging conformation based on the desired downsized shape where the regurgitation of the valve is reduced, and the distal curvilinear shaped portion has a delivery shape based on a shape of the dilated valve annulus shape, wherein the delivery shape has a dimension that is larger than the tissue engaging conformation of the annuloplasty implant, and mounting the annuloplasty implant resiliently in the hollow in the delivery shape before releasing from the hollow.

Advantageously, the delivery device comprises a sizing actuator, for reducing the distal curvilinear shaped portion from the delivery shape by the actuator.

Advantageously, the procedure includes restraining the anchoring elements in the restrained spring loaded delivery positiOn with a first restraining unit for, and releasing the anchoring elements by releasing the first restraining unit for anchoring the anchoring elements into the annulus.

Advantageously, the procedure includes restraining the annuloplasty implant in the hollow of the distal curvilinear shaped portion with a second restraining unit, and demounting the annuloplasty implant from the hollow upon releasing the second restraining unit, wherein the second restraining unit preferably is only demounted when a correct position of the annuloplasty implant is confirmed, allowing for removing the annuloplasty implant from the annulus if correct position of the annuloplasty implant is not confirmed, and avoiding undesired embolization of the annuloplasty implant.

Advantageously, the procedure includes restraining the annuloplasty implant in the hollow of the distal curvilinear shaped portion with a third restraining unit for mounting the annuloplasty implant in the hollow of the distal curvilinear shaped portion, thus preventing an undesired release of the annuloplasty implant from the hollow.

Advantageously, the procedure includes a system having the first, second and third restraining unit, wherein the third restraining unit is releasing the annuloplasty implant by withdrawing the delivery device when the first restraining unit has released the anchoring elements from the restrained spring loaded delivery position and anchored the anchoring elements into the annulus tissue.

Further embodiments of the invention are defined in the dependent claims, wherein features for the second and subsequent aspects of the invention are as for the first aspect mutatis mutandis.

Advantageously, a mitral valve repair system is provided comprising a delivery tool and an annuloplasty curvilinear shaped structure for transluminal delivery. The delivery device comprises a hollow for the annuloplasty curvilinear shaped structure. The annuloplasty curvilinear shaped structure is positioned with the opening of the hollow of the tool oriented towards the annulus to be affixed thereto. The annuloplasty curvilinear shaped structure has anchoring elements that are released into the tissue of the annulus thus anchoring the curvilinear shaped structure in the tissue. The anchoring elements are e.g. hooks resiliently kept in a position away from the tissue, then released, e.g. by removing a restraining wire, digging into the tissue. The delivery tool is then removed It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
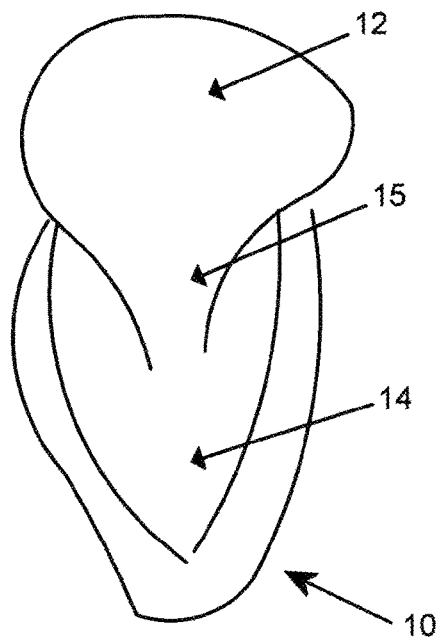
FIG. 1 is a schematic illustration of a portion of a heart 10 including a left ventricle 14, a left atrium 12 and a mitral valve 15.
Figure 2:
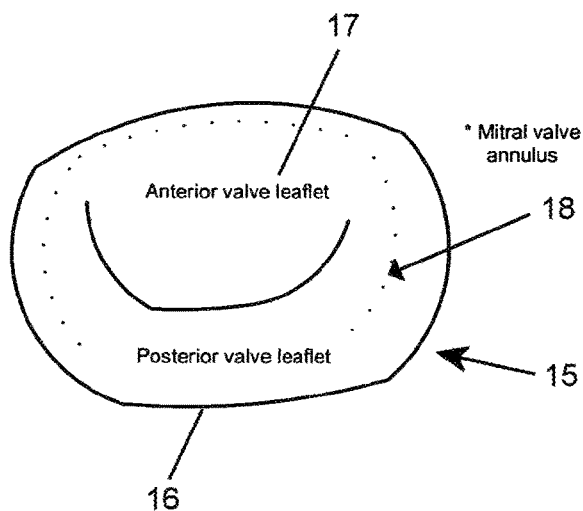
FIG. 2 is a schematic illustration of a mitral valve 15 having an anterior valve leaflet 17 and a posterior valve leaflet 16.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In an embodiment of the invention according to the Figures, a catheter 4 based medical system 1 for reducing cardiac valve regurgitation is shown. The system 1 has a resilient and/or elastic curvilinear shaped structure annuloplasty implant 3 for reducing the size of a dilated annulus 18 of the valve for reducing the regurgitation having resilient anchoring elements 300. The anchoring elements 300 may be provided as barbs or hooks.

The system further has a delivery device 2 for the annuloplasty implant 3 having a distal curvilinear shaped portion 200 that is hollow to Mount the annuloplasty implant 3 and has an annular opening 201 arranged to be in apposition against an annulus 18 of the cardiac valve. The annuloplasty implant 3 is mounted to be releasable in the hollow and has the resilient anchoring elements 300 arranged in a restrained spring loaded delivery conformation in the hollow, and wherein the resilient anchoring elements 300 when unrestrained, are arranged in a tissue engaging conformation protruding out of the opening.

The number of anchoring elements, depth of anchoring elements, etc. may be chosen to effectively treat the valve leakage and reliably anchor the annuloplasty implant to the surrounding tissue. The length of an anchoring element is not limited by other anchoring elements. Thus, relatively long anchoring elements may be provided resulting in a deep tissue anchoring of the implant.

Anchoring elements 300 may be formed integrally with the annuloplasty implant 3. The implant 3 and the anchoring elements 300 may be formed as a monolithic structure. Alternatively the anchoring elements 300 may be affixed to the annuloplasty implant 3, e.g. by welding, gluing etc. Some of the anchoring elements 300 may be part of a collar (not shown) surrounding the annuloplasty implant 3. The collar may be a fabric collar to improve sealing and/or ingrowth of the implant when implanted. The collar may also provide for an effective assembly of the annuloplasty implant 3 and the anchoring elements 300 by means of the collar. Alternatively, the anchoring elements may protrude radially through the collar at their positions along the implant. In the latter case, such anchoring elements may be positioned outside of the collar element, originating from the annuloplasty implant 3 arranged therein.

Thus, in embodiments, medical devices are provided for reducing cardiac valve regurgitation. The device includes an elongate resilient curvilinear shaped annuloplasty implant 3 for reducing the size of a dilated annulus of the valve for reducing the regurgitation. The annuloplasty implant has resilient anchoring elements 300 protruding radially outwards from the annuloplasty implant 3. The anchoring elements are arrangeable in a spring loaded first radial direction for delivery, and when released from the delivery position anchor the annuloplasty implant to tissue at the annulus in a second radial direction, different from the first radial direction. This is illustrated in FIGS. 5 and 6A-6D.

Multiple of the anchoring elements may be arranged at different radial positions around the cross section of the annuloplasty implant. In the Figures it is illustrated that the anchoring elements 301, 302 are arranged as pairs opposite each other. Multiple anchoring elements are shown arranged at the same longitudinal position on the annuloplasty implant. Alternatively or in addition, the anchoring elements may be arranged at different radial positions as single elements at different longitudinal positions (not shown). This allows for flexibility and a reliable anchoring of the annuloplasty implant, e.g. in dependence of anatomical structures that should be avoided to be penetrated by anchoring elements, such as blood vessels.

Figure 3:
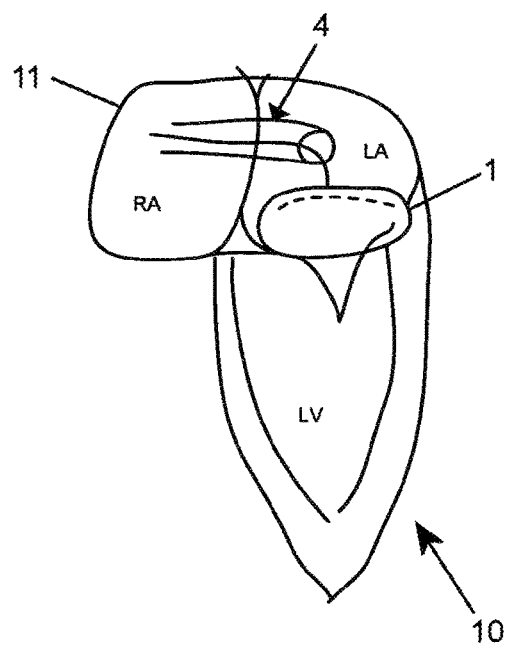
FIG. 3 is a schematic illustration of a portion of a heart 10 including right atrium 11, a catheter 4 and a medical system 1.

The system is minimally invasive deliverable via a transluminal catheter 4, as shown in FIG. 3.

The resilient curvilinear shaped annuloplasty implant 3 has a tissue engaging conformation based on a desired downsized shape where the regurgitation of the valve is reduced, and the distal curvilinear shaped portion 200 has a delivery conformation based on a shape of the dilated valve annulus shape, wherein the delivery shape has a dimension that is larger than the tissue engaging conformation of the annuloplasty implant 3, such that the annuloplasty implant 3 is resiliently kept in the hollow 201 in the delivery conformation before demounting from the hollow.

In some embodiments the delivery device may a sizing actuator (not shown), and wherein the distal curvilinear shaped portion 200 is reducible from the delivery conformation by the actuator. In this manner, the delivery device 3 or tool may be affixed to the annuloplasty curvilinear shaped structure 2 during the downsizing step before releasing the curvilinear shaped structure 3 from the tool, and after affixing the curvilinear shaped structure 3 to the annulus tissue by means of the attachment units 300. In this manner, the curvilinear shaped structure 3 is readily retrievable from the cardiac valve in case the positioning thereof is not satisfactory, e.g. as detected via ultrasound based examination of the positioning result.

Figure 6A:
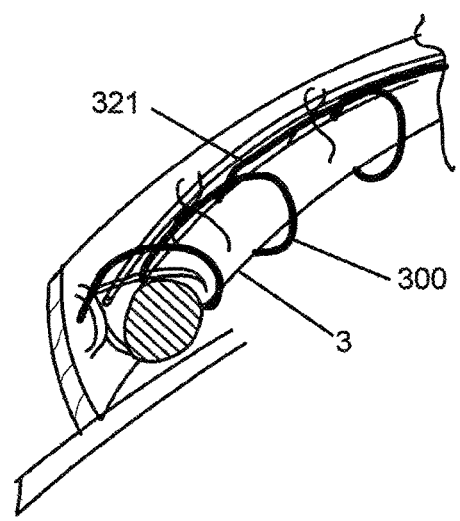
FIGS. 6A-6D are a elevated, partly cross sectional vie (6A), and sectional views, FIGS. 6C and 6D at A (in FIG. 5) and FIG. 6B at B, of a distal portion of the aggregate of FIG. 5, respectively.
Figure 6B:
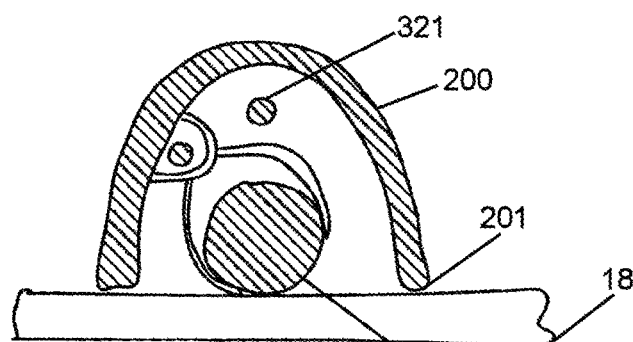
Figure 6C:
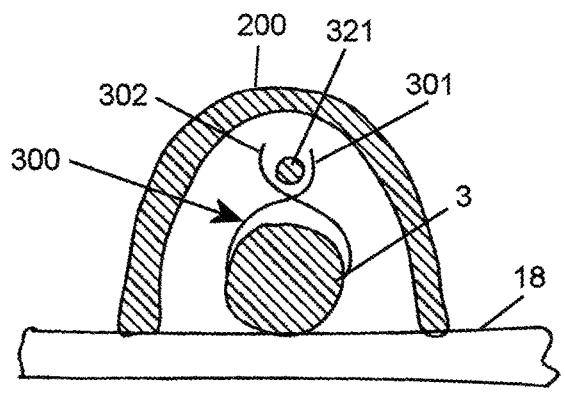

As e.g. shown in FIGS. 5, 6A, 6B and 6C, the delivery device 2 has a first restraining unit 321 for restraining the anchoring elements 300 in the restrained spring loaded delivery conformation. The first restraining unit 321 may be a wire against which the anchoring elements 300 are spring loaded, as illustrated. The wire may alternatively be guided through loops 320 inside the hollow (FIG. 6A).

The delivery device 2 has a second restraining unit 221 for restraining the annuloplasty implant 3 in the hollow of the distal curvilinear shaped portion 200. The second restraining device is shown as a tethered line holding the curvilinear shaped structure 3 in the hollow against loop eyes 220. In this manner, additional security is provided as the implant may be retracted when it is still restrained to the delivery device by means of the second restraining unit 221. Thus e.g. embolization of the device is avoided, which otherwise would make a surgical retrieval procedure necessary, likely including open chest surgery with all its disadvantages.

In the illustrated embodiment the delivery device 2 further has a third restraining unit 210 for keeping the annuloplasty implant 3 in the hollow of the distal curvilinear shaped portion 200. The third restraining unit 210 has two arms 210, 212 that hold the curvilinear shaped structure 3 in the hollow. The second restraining device may be omitted. When the curvilinear shaped structure has anchoring elements 300 deployed in the annulus, the third restraining units are provided with such a holding force, that a retraction of the delivery device 2 will release the latter from the curvilinear shaped structure 3.

In the embodiment having the first, second and third restraining units, the third restraining unit 210 is arranged to release the annuloplasty implant 3 by withdrawing the delivery device 2 when the first restraining unit has released the anchoring elements 300 from the restrained spring loaded delivery conformation and anchored the anchoring elements 300 into the annulus tissue.

In the illustrated embodiment the cardiac valve is a mitral valve 15, and the system is facilitating transseptal percutaneous delivery into the left atrium to the atrial side of the mitral valve. A delivery portion 202 of the delivery device 2 is distally connected to the distal curvilinear shaped portion 200 and has a distal curvature to allow access from a septal opening towards the mitral valve. The transition may be provided as shown. Alternatively, several arms may be provided at the transition to the hollow. The delivery portion 202 may be tubular hollow In some embodiments the cardiac valve is the tricuspid valve, and the system is adapted for percutaneous delivery into the right atrium to the atrial side of the tricuspid valve, and a delivery portion 202 of the delivery device 2 is distally connected to the distal curvilinear shaped portion 200 and has a distal curvature to allow suitable access towards the tricuspid valve.

Figure 4:
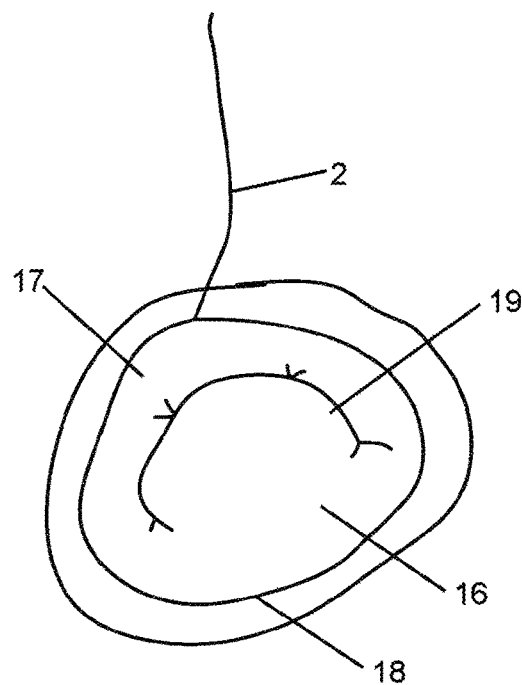
FIG. 4 is a schematic illustration of a delivery device 2 arranged and pushed down on a mitral valve annulus 18, wherein the valve is dilated as seen at the opening 19 between the leaflets 16, 17.
Figure 5:
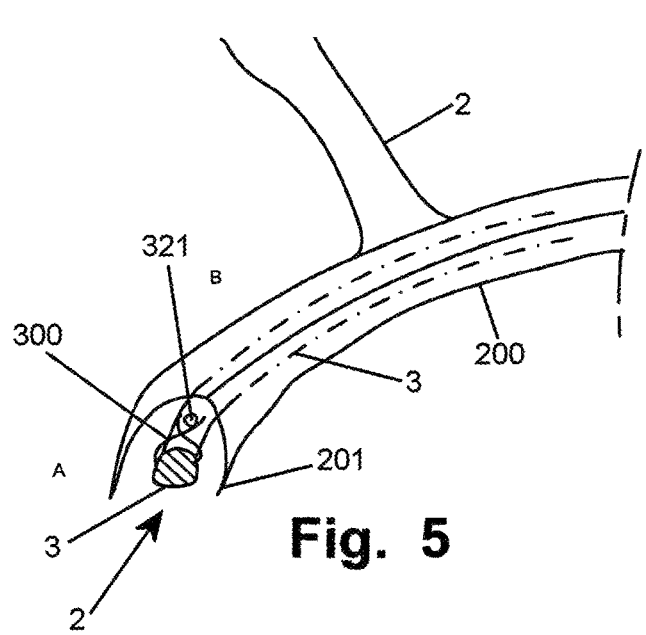
FIG. 5 is a schematic illustration of an aggregate of a delivery device 2 and the annuloplasty curvilinear shaped structure 3.

Access of catheter 4 or a similar guide is provided to the left atrium, and is e.g. achieved by positioning the catheter 4 in central or peripheral veins, thereby achieving access to the right atrium. In such a situation, the tricuspid valve (not shown) may be accessed from above the valve. The tricuspid valve is alternatively accesses via other vessels, e.g. the jugular vein, for access from above. Then a standard atrial trans-septal approach may be utilized to access the left atrium by creation of an iatrogenic atrial septal defect (ASD). In such a situation, the mitral valve may be accessed from above the valve, see e.g. FIG. 3 and FIG. 4.

In some embodiments the hollow of the distal curvilinear shaped portion 200 is provided with a negative pressure for suction of the hollow to the annulus. The pressure may e.g. be provided through the hollow delivery portion 202 when the latter has a lumen distally connected to the hollow at the junction thereof. Alternatively, or in addition, separate lumen may be provided for fluid communication with the hollow. A pressure generator is in these embodiments arranged proximally, outside the patient. The pressure in the hollow may be measured. Thus a contact with the annulus tissue is determinable from the measured pressure or an energy consumption of a flow generator generating the pressure. This improves reliability, patient safety, and user acceptance of the system and procedure considerably.

In some embodiments, alternatively or additional to the entire hollow of the curvilinear shaped portion 200 being provided with a negative pressure for suction of the hollow to the annulus, discrete suction units (not shown in the figures) are provided at that portion 200.

The distal portion may thus comprise a plurality of suction units for providing and/or determining a desired apposition of the distal portion at the target tissue prior to releasing the medical implant to the tissue and retracting the delivery device.

In some embodiments, the suction units are provideable with a negative pressure for suction to the tissue, and wherein the medical implant is not releasable before all suction units are confirmed in apposition with the tissue.

In some embodiments, the plurality of suction units are distributed along a periphery of the distal portion.

In some embodiments, a firm seat at the tissue is confirmed by an absence of a reflow of blood from the suction units.

In some embodiments, the suction units are arranged to provide for a symmetric delivery of the implant when release to the tissue.

In some embodiments, the tissue is a cardiac valve annulus and the implant is an annuloplasty implant, such that the distal portion is arrangeable for a synchronous and simultaneous reshaping procedure of the annulus by the implant.

In some embodiments the distal curvilinear shaped portion 200 has arranged thereon a sensor (not shown) for indicating contact with the annulus tissue, such as a piezo transducer. The senor is preferably integrated into the edge of the distal curvilinear shaped portion 200, oriented towards the annulus. In this manner, a clear difference can be identified between blood and valve tissue. This improves reliability, patient safety, and user acceptance of the system and procedure considerably. In addition, the correct seating and positioning of the curvilinear shaped structure 3 and the delivery device may be checked with other measurements, e.g. ultrasonic imaging based measurements.

In some embodiments the distal curvilinear shaped portion 200 has at least one fiducial marker. The fiducial marker may be arranged at a periphery of the distal curvilinear shaped portion 200; and/or wherein one of the fiducial markers is an annular fiducial marker arranged along the periphery. A plurality of fiducial markers may be distributed along the distal curvilinear shaped portion 200 for identifying the distal curvilinear shaped portion 200 inside a body of a patient having the cardiac valve. The fiducial markers may e.g. be air filled gaps in the wall of the distal curvilinear shaped portion 200. The fiducial markers may be made integrally with the distal curvilinear shaped portion 200.

Figure 8:
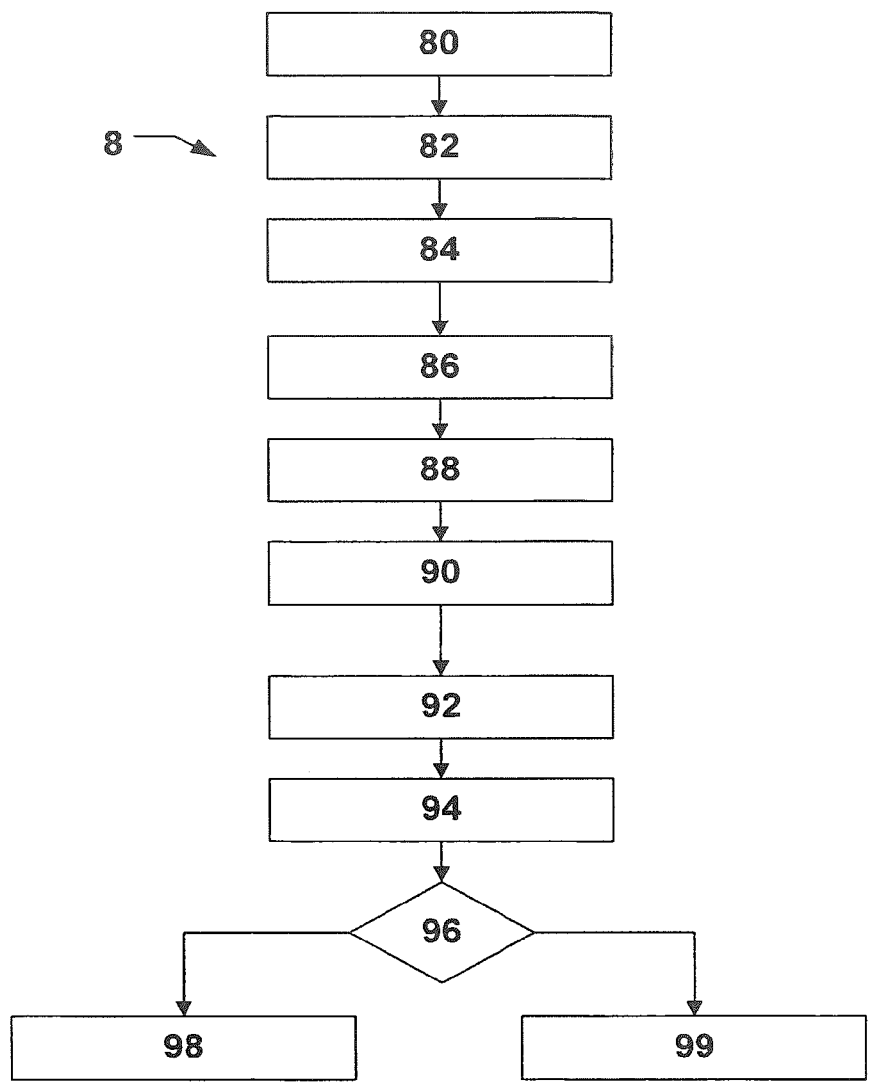
FIG. 8 is a flowchart illustrating a medical procedure.

As illustrated in FIG. 8 a medical procedure 8 for reducing cardiac valve regurgitation is now described. The procedure comprises the steps described hereinafter.

The geometry of a dilated cardiac valve of a patient including the shape and size of a dilated annulus thereof is measured 80.

Then a downsized shape and size of the annulus is determined. The procedure continues with selecting 84 a resilient annuloplasty implant having in a tissue engaging conformation a shape and size to be arranged at the downsized annulus based on the determined downsized shape and size of the annulus. This may be done in a virtual environment, planning the delivery of a patient adapted annuloplasty curvilinear shaped structure 3. The patient adapted annuloplasty curvilinear shaped structure 3 may be produced from manufacturing data output from the virtual planning. Alternatively, an annuloplasty curvilinear shaped structure 3 may be chosen from a library of pre-manufactured curvilinear shaped structures 3. In more detail, a method of virtually planning an annuloplasty implantation for a medical procedure may comprise, performing in a computer environment, an image based, such as ultrasonic based, measuring of a geometry of a dilated cardiac valve. This is based on patient image data. Further, the virtual planning may comprise determining a reduction of a regurgitation of the valve when downsizing the annulus of the dilated valve. The determining may be based on a simulation algorithm emulating the patient tissue performance in the computer environment. Moreover, the planning includes selecting a patient adapted shape and size of a resilient annuloplasty implant 3 for a tissue engaging conformation to be arranged at the downsized annulus based on the determined downsized shape and size of the annulus. From this planning, production data may be provided for the annuloplasty implant 3, components thereof, and/or a delivery system thereof. In a method of producing a medical device the production data obtained by the virtual planning may be used for producing the element(s). Production may be done my rapid prototyping techniques, or other manufacturing methods that the skilled person will be aware of in the present context.

The procedure then continues with introducing 86 the annuloplasty implant in a delivery device 3 in a compressed state via a catheter to the cardiac valve. The annuloplasty curvilinear Shaped structure may e.g. be stretched into an elongate configuration to fit into catheter 4 for delivery.

When the distal end of the catheter is at the release site at the valve, the procedure continues with releasing 88 an aggregate of a distal portion of the delivery device and the annuloplasty implant in a stretched state in the delivery device from the catheter such that implant resumes an expanded shape. The expanded shape is determined by the delivery device shape and size, and the annuloplasty curvilinear shaped structure 3 is expanded in relation to its tissue engaging conformation. The expanded shape corresponds to the shape of the dilated cardiac valve, allowing for easy positioning of the aggregate.

Then the procedure includes positioning 90 the aggregate at the annulus, e.g. by pushing against the annulus as shown in FIGS. 4, 6A-6D, and 7A,B.

Figure 6D:
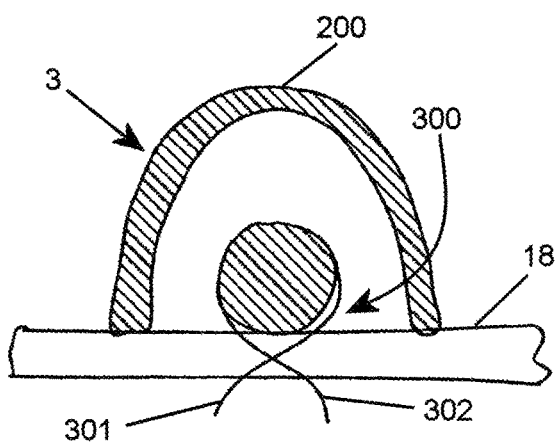
Figure 7A:
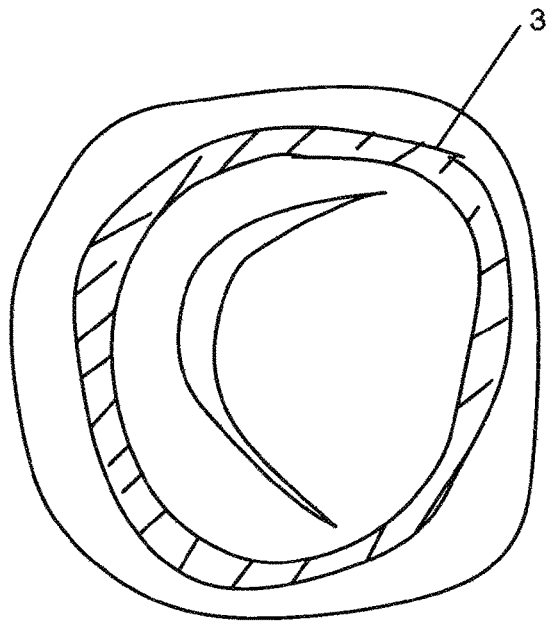
FIGS. 7A-7C illustrate the example of delivery of an annuloplasty curvilinear shaped structure 2 by means of a delivery device 3 to a mitral valve and downsizing of the valve.
Figure 7B:
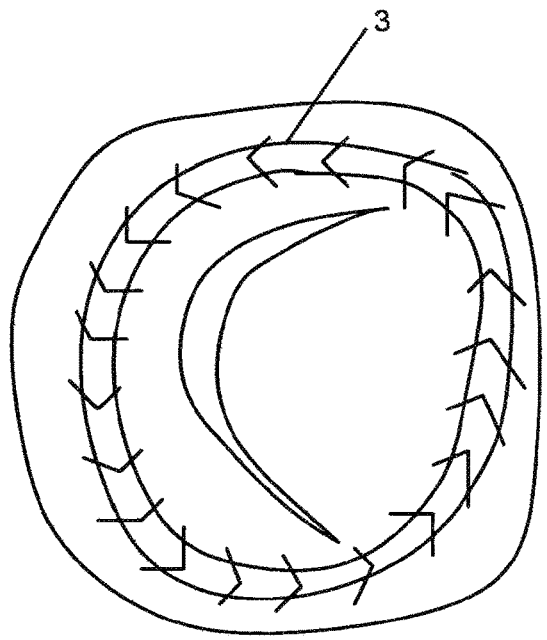
Figure 7C:
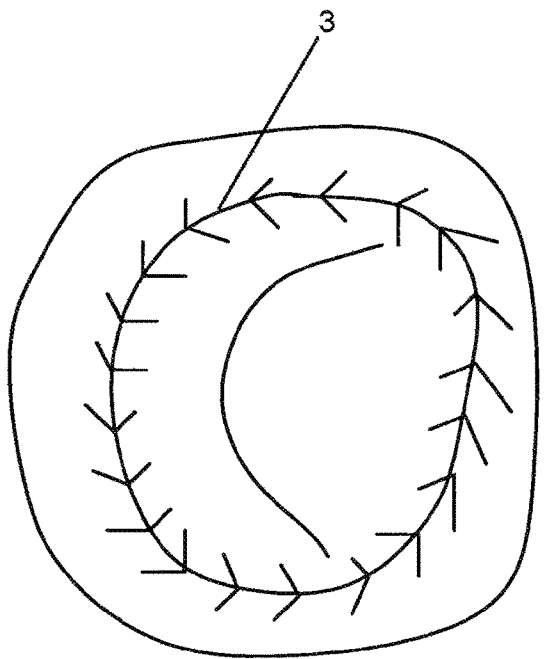

The aggragate may be fixated to the annulus by activating suction of suction units. P providing and/or verifying a desired apposition of the distal portion at the annulus prior to releasing the implant The anchoring elements 300 of the annuloplasty implant are released and are anchoring the anchoring elements into the annulus (FIGS. 6D, 7B).

Alternatively, or in addition to the anchoring elements described herein, the implant may be permanently affixed to the tissue by sutures, e.g. using a transcatheter deliverable suturing unit, which does not need to be described in more detail herein.

Then the shape or size of the delivery device and/or annuloplasty implant is reduced for reshaping the annulus to the downsized shape; determining 96 a reduction of the cardiac valve regurgitation; and removing 98 the delivery device and catheter if the reduction is satisfactory, or removing 99 the annuloplasty implant together with the delivery device when the reduction is determined as not being satisfactory.

In some embodiments the procedure includes ultrasonic measurement for the measuring 80 a geometry of the dilated cardiac valve, and/or the determining 96 a reduction of the cardiac valve regurgitation.

In some embodiments the procedure further includes subsequently to the positioning 90 the aggregate at the annulus: determining a position of the delivery device at the annulus, and repositioning the delivery device and annuloplasty implant.

In some embodiments the procedure includes applying a catheter 4 based medical system 1 for reducing the cardiac valve regurgitation, having the resilient curvilinear shaped annuloplasty implant 3 for reducing the size of a dilated annulus 18 of the valve for reducing the regurgitation having resilient anchoring elements 300, and a delivery device 2 for the annuloplasty implant 3 having a distal curvilinear shaped portion 200 that is hollow in which to mount the annuloplasty implant 3 and has an annular opening 201 arranged to be in apposition against an annulus 18 of the cardiac valve; the procedure comprising arranging the annuloplasty implant 3 to be releasable in the hollow with the resilient anchoring elements 300 arranged in a restrained spring loaded delivery conformation in the hollow, for the introducing 86 and releasing 88;

The resilient anchoring elements 300 are unrestrained by withdrawing the restraining unit 321. Thus the anchoring elements 300 are moving into the tissue of the adjacent annulus and the resilient anchoring elements 300 are arranged in a tissue engaging conformation protruding out of the opening into the annulus to be released 92. The annulus curvilinear shaped structure 30 is thus anchored to the annulus' 18 tissue of the cardiac valve, but still affixed to the delivery device. The delivery device may then be removed by releasing the second and/or third restraining unit. Alternatively, the aggregate may be retracted if so desired.

The procedure is a minimally invasive procedure.

The resilient curvilinear shaped annuloplasty implant 3 has in embodiments a tissue engaging conformation based on the desired downsized shape where the regurgitation of the valve is reduced, and the distal curvilinear shaped portion 200 has a delivery conformation based on a shape of the dilated valve annulus shape, wherein the delivery conformation has a dimension that is larger than the tissue engaging conformation of the annuloplasty implant 3, and mounting the annuloplasty implant 3 resiliently in the hollow 201 in the delivery conformation before releasing from the hollow.

In some embodiments the delivery device comprises a sizing actuator, and reducing the distal curvilinear shaped portion 200 from the delivery conformation by the actuator.

In some embodiments the procedure includes restraining the anchoring elements 300 in the restrained spring loaded delivery position with a first restraining unit 321 for, and releasing the anchoring elements 300 by releasing the first restraining unit 321 for mounting the anchoring elements into the annulus.

In some embodiments the procedure includes restraining the annuloplasty implant 3 in the hollow of the distal curvilinear shaped portion 200 with a second restraining unit 221, and releasing the annuloplasty implant 3 from the hollow upon releasing the second restraining unit, wherein the second restraining unit preferably is only released when a correct position of the annuloplasty implant is confirmed, allowing for removing the annuloplasty implant from the annulus if correct position of the annuloplasty implant is not confirmed, and avoiding undesired embolization of the annuloplasty implant.

In some embodiments the procedure includes restraining the annuloplasty implant 3 in the hollow of the distal curvilinear shaped portion 200 with a third restraining unit 210 for keeping the annuloplasty implant 3 in the hollow of the distal curvilinear shaped portion 200, thus preventing an undesired release of the annuloplasty implant 3 from the hollow.

In some embodiments the procedure includes a system having the first, second and third restraining unit, wherein the third restraining unit 210 is releasing the annuloplasty implant 3 by withdrawing the delivery device 2 when the first restraining unit has released the anchoring elements 300 from the restrained spring loaded delivery conformation and anchored the anchoring elements 300 into the annulus tissue.

In some embodiments the procedure includes making a transseptal puncture in the heart; wherein the cardiac valve is a mitral valve, and wherein the introducing 86 is a transseptal percutaneous delivery into the left atrium to the atrial side of the mitral valve, and wherein a delivery portion 202 of the delivery device 2 is distally connected to the distal curvilinear shaped portion 200 and has a distal curvature to allow access from a septal opening towards the mitral valve.

In some embodiments the procedure includes making a transseptal puncture in the heart; wherein the cardiac valve is tricuspid valve, and wherein the system is adapted for percutaneous delivery into the right atrium to the atrial side of the tricuspid valve, and wherein a delivery portion 202 of the delivery device 2 is distally connected to the distal curvilinear shaped portion 200 and has a distal curvature to allow suitable access into the atrium towards the tricuspid valve.

In some embodiments the procedure includes generating a negative pressure in the hollow of the distal curvilinear shaped portion 200 for suction of the hollow to the annulus. The procedure may include measuring the pressure in the hollow and determining a contact with the annulus tissue from the measured pressure or an energy consumption of a flow generator generating the pressure.

In some embodiments the procedure includes indicating contact with the annulus tissue with a sensor arranged on the distal curvilinear shaped portion 200, such as based on sound waves emitted and received from a piezo transducer, such as an ultrasonic transducer.

In some embodiments the procedure includes identifying the distal curvilinear shaped portion 200 inside a body of a patient having the cardiac valve by means of detecting at least one fiducial marker of the delivery device, such as a plurality of fiducial markers distributed along the distal curvilinear shaped portion 200 for the identifying and/or a fiducial marker that is arranged at a periphery of the distal curvilinear shaped portion 200, and/or wherein one of the fiducial marker is an annular fiducial marker arranged along the periphery.

Some embodiments of the invention provide for an alternative system and method of reducing cardiac valve regurgitation. Some embodiments of the invention provide for catheter based minimally invasive procedure in accordance with clinical procedures for accessing an atrium. Clinical personal has thus not to be trained with completely new access procedures to the atrium and will readily learn to apply the inventive concept described herein.

By means of an atrial delivery path approach, navigation and fixation of a distal portion of the delivery device, prior to release of the implant, a symmetrical implantation of the implant is provided. A synchronous and simultaneous reshaping procedure is provided.

This is a major progress in the minimally invasive implantation of annuloplasty implants. A reliable implantation is provided. As reshaping is done synchronous and simultaneous upon release of the implant from the distal portion of the delivery device, any tensions or undesired tissue movements are avoided that would need to be corrected by surgical interventions. As additionally, a patient specific implant may be provided and the procedure may be computer simulated in advance of the real medical procedure, results are improved considerably while the procedure is simplified.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A medical procedure for reducing cardiac valve regurgitation including the steps of:
   measuring the geometry of a dilated cardiac valve of a patient including the shape and size of a dilated annulus thereof;
   determining the downsized shape and size of said dilated annulus;
   selecting a resilient annuloplasty implant having in a tissue engaging conformation a shape and size to be arranged at said dilated annulus based on said determined downsized shape and size of said dilated annulus;
   introducing said annuloplasty implant in a delivery device in a compressed state via a catheter to said dilated cardiac valve;
   releasing an aggregate of a distal portion of said delivery device and said annuloplasty implant in a stretched state in said delivery device from said catheter such that said annuloplasty implant assumes an expanded shape;
   positioning said aggregate at said dilated annulus;
   affixing said distal portion to said dilated annulus by activating suction of suction units;
   providing and/or verifying a desired apposition of said distal portion at said dilated annulus prior to releasing said annuloplasty implant;
   releasing and anchoring said annuloplasty implant into said dilated annulus;
   reducing the size of said delivery device and/or annuloplasty implant for reshaping said dilated annulus to said downsized shape;
   determining a reduction of said dilated cardiac valve regurgitation, and
   removing said delivery device and catheter if the reduction is satisfactory, or removing said annuloplasty implant together with said delivery device when said reduction is determined as not being satisfactory; and including
   applying a catheter-based medical system for reducing said cardiac dilated cardiac valve regurgitation, said medical system having said annuloplasty implant for reducing the size of said dilated annulus of said dilated cardiac valve for reducing said regurgitation, and a delivery device for said annuloplasty implant having a distal hollow portion for receiving said annuloplasty implant and having an opening arranged to be in opposition against said dilated annulus of said dilated cardiac valve; said procedure further including releasably mounting said annuloplasty implant in said distal hollow portion with said resilient anchoring elements arranged in a restrained spring loaded delivery conformation in said hollow, for said introducing;

positioning said aggregate at said dilated annulus;

providing and/or verifying a desired apposition of said distal portion at said dilated annulus prior to releasing said annuloplasty implant;

releasing and anchoring said annuloplasty implant into said dilated annulus.

2. The procedure of any of claim 1, including restraining said annuloplasty implant in said distal hollow portion with a second restraining unit, and releasing said annuloplasty implant from said hollow upon releasing said second restraining unit, wherein said second restraining unit preferably is only released when a correct position of said annuloplasty implant is confirmed, allowing for removing said annuloplasty implant from said dilated annulus if the correct positioning of said annuloplasty implant is not confirmed, and avoiding undesired embolization of said annuloplasty implant.

3. The procedure of claim 1, including generating a negative pressure in a plurality of suction units of said distal portion for suction of said distal portion to said dilated annulus, and measuring said negative pressure and determining a contact of said suction units with said dilated annulus tissue from said measured pressure or an energy consumption of a flow generator generating said pressure.

4. The procedure of claim 3, including indicating contact with said dilated annulus tissue with a sensor arranged on said distal portion based on sound waves emitted and received from a piezo transducer.

5. The procedure of claim 1, including identifying said distal portion inside a body of a patient having said dilated cardiac valve by means of detecting at least one fiducial marker of said delivery device.

6. The procedure of claim 5, including identifying a plurality of fiducial markers distributed along said distal portion.

7. The method of claim 5, including identifying at least one fiducial marker that is arranged at a periphery of said distal portion, and/or identifying at least one an annular fiducial marker arranged along said periphery.

* * * * *